United States Patent [19]

Green

[11] 4,078,180
[45] Mar. 7, 1978

[54] X-RAY INSPECTION OF WELDS

[75] Inventor: Donald T. Green, Mentor, Ohio

[73] Assignee: United States Steel Corporation, Pittsburgh, Pa.

[21] Appl. No.: 667,925

[22] Filed: Mar. 17, 1976

[51] Int. Cl.² .............................................. G01N 23/00
[52] U.S. Cl. ............................. 250/358 R; 250/358 P
[58] Field of Search ............... 250/358 P, 358 R, 359, 250/360, 358 T, 483

[56] References Cited

U.S. PATENT DOCUMENTS

| | | | |
|---|---|---|---|
| 3,521,059 | 7/1970 | Stolle | 250/358 P |
| 3,569,708 | 3/1971 | Weinbaum et al. | 250/358 P |
| 3,686,932 | 8/1972 | Ries et al. | 250/358 P |
| 3,903,416 | 9/1975 | Fox | 250/358 T |
| 3,917,950 | 11/1975 | Carlson | 250/483 |

*Primary Examiner*—Davis L. Willis
*Attorney, Agent, or Firm*—Harold S. Meyer

[57] ABSTRACT

X-ray equipment for nondestructive testing and particularly for mechanized testing of the integrity of welds along the length of the welds includes means for mechanically traversing an X-ray source along one side of the weld and a grainless fluorescent screen along the other side, with the screen coupled to an image-isocon video camera, preferably through a light intensifier. The equipment includes means for display of the X-ray shadow picture from the video camera and for superimposing identifying indicia, along with means for recording the composite of the indicia and the picture. The image is preferably integrated over at least several frames so as to minimize "noise" and intensify contrast. In addition, a signal from an ultrasonic transducer may be provided to indicate to the operator the existence of a probable flaw in the weld metal.

15 Claims, 6 Drawing Figures

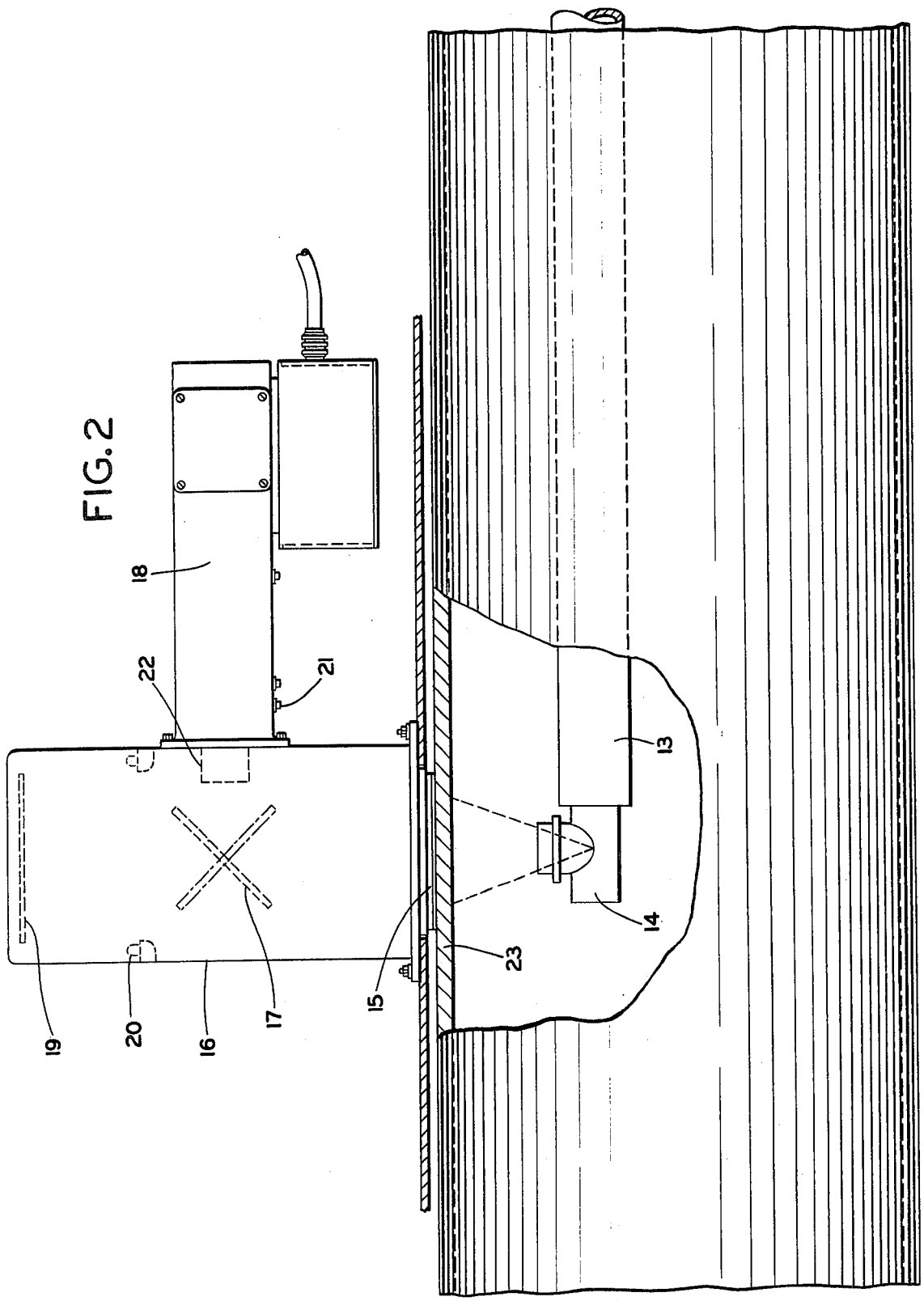

X-RAY INSPECTION OF WELDS

BACKGROUND

X-ray equipment has been extensively used for nondestructive testing of various products including the inspection of welds to locate voids and other flaws which might lead to failure of the welded product. Such inspection has been required for acceptance of large diameter pipe for high pressure transportation of hazardous materials such as gas and oil fuels, but has been very slow and expensive because of the time required for making each of a sequence of photographs of the X-ray shadow picture.

The object of this invention accordingly is to automate the inspection of welds and at the same time to decrease the time and cost required and increase the precision of the operation.

Another object is to provide equipment which can be coordinated with other inspection techniques, such as ultrasonic monitoring.

SUMMARY OF THE INVENTION

This invention consists of a combination of elements which together provide for rapid and inexpensive inspection with a minimum of human labor. The invention is preferably used in connection with automatic equipment for relative movement of the test objects with respect to the testing devices along the entire length of the weld.

The invention is particularly adapted to the inspection of longitudinal welds in high pressure steel pipe for long distance pipe lines. Thus, when the invention is used for inspection of such pipe, a known type of manipulating equipment may be used for lengthwise traverse of a section of pipe surrounding a boom on the end of which is an X-ray source. Opposite the X-ray source, on the outside of the pipe, is a particular kind of video camera including a fluorescent screen of high brilliance and an image-isocon camera for translation of the visible light image on the fluorescent screen into an electronic image of high intensity and resolution.

The equipment also includes a monitor where the X-ray image is presented to an operator as well as a photofluorographic unit for making a permanent photographic record of any desired portion or all of the length of the weld.

Preferably the equipment includes also an ultrasonic inspection device which is capable of warning the operator of the presence of an irregularity in the weld.

Accordingly, the equipment of this invention, particularly when combined with suitable object manipulating machines and ultrasonic equipment, provides for a previously unattainable economy and precision of inspection and location of defects which require correction.

THE DRAWINGS

In the accompanying drawings,

FIG. 2 is a partial section on a larger scale showing the relative positions of the preferred X-ray tube and camera of this invention when used for inspection of longitudinal pipe welds.

DETAILED DESCRIPTION

Figure 1:
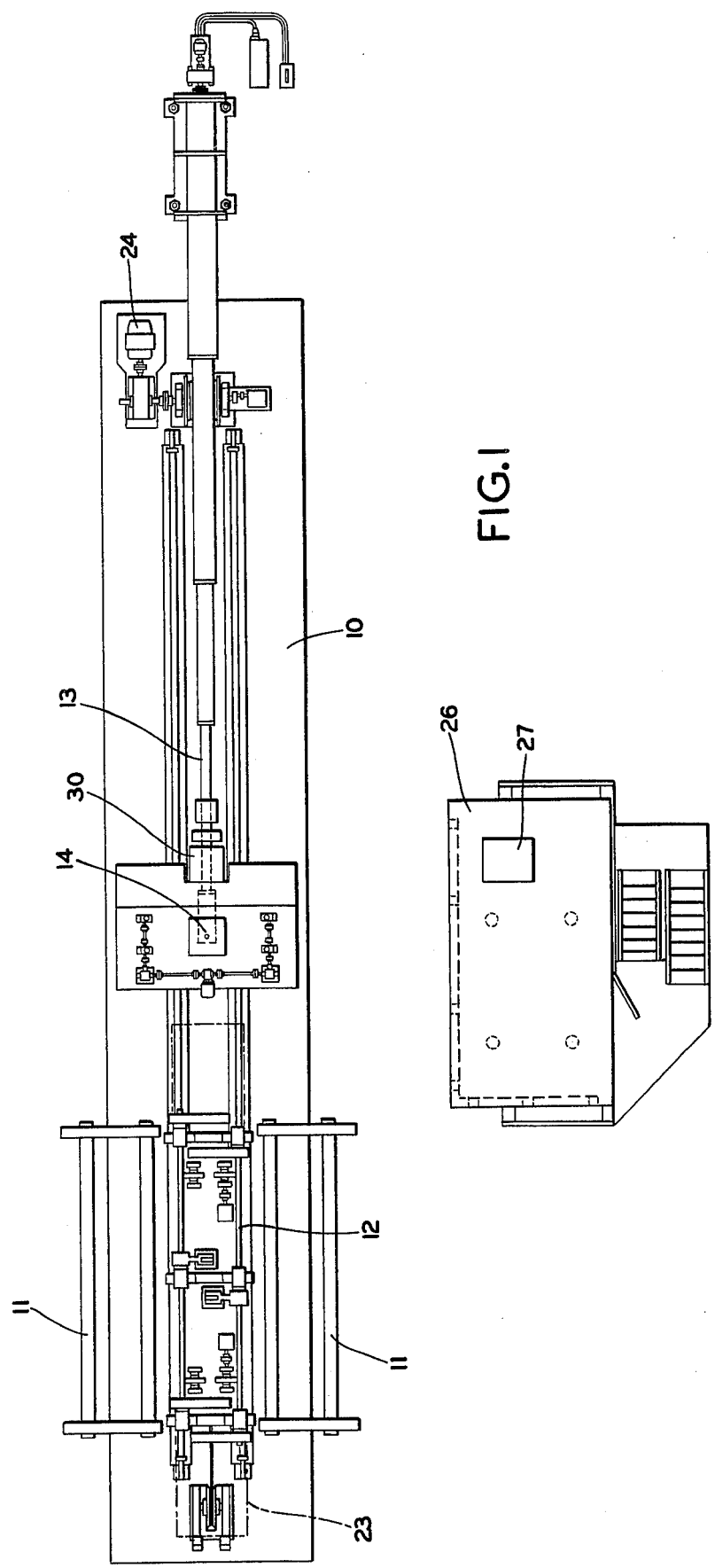
FIG. 1 is a general plan view of an installation for automated inspection of large diameter pipe.

In FIG. 1 mechanized equipment for handling of sections of large diameter thick-walled pipe is shown in a schematic plan view. At one end on a suitable base 10 are mounted load and unload tables 11 from and to which the pipe sections are brought by a longitudinally movable pipe carriage 12 which is capable of transporting each section of pipe in turn lengthwise past the inspection elements of the machine and then quickly returning them to the loading point for discharge and reception of another section of pipe.

The pipe carriage 12 is power driven lengthwise as by motor 24 which includes or is coupled to a pulse generator for indicating the extent of motion, or momentary location, of the pipe 23.

At the other end of the machine, a rigid boom 13 is received inside of the pipe as the pipe is advanced lengthwise by motion of the carriage. At the end of the boom 13 is mounted a source of pentrating radiation such as X-rays, gamma rays, or even neutron rays or cathode rays. Preferably X-rays are used since they are easily controllable at high intensities which permit rapid inspection. The boom 13 and the radiation source such as X-ray tube 14 are vertically adjustable for proper positioning in difference sizes of pipe. In this preferred arrangement, the radiation is directed vertically upward.

Best results have been obtained with a ceramic X-ray tube operating at up to 160 KV, having a dual focal spot, with a beryllium window, and with the X-ray beam collimated to a cone of approximately 40° width. With a small 0.4 mm focal spot, it may be operated at 10 MA (milliamperes) at a moderate voltage or up to 4 MA at the maximum 160 KV. With a large 3 mm focal spot, it may be operated at 40 MA at a moderate voltage or up to 19 MA at the maximum 160 KV.

FIG. 2 shows, on a larger scale, the position of the X-ray tube 14 with the conical X-ray beam projected upward through the weld in the wall of the pipe 23.

On the outside of the pipe facing the X-ray tube 14 is a high brilliance fluoroscopic screen 15, preferably a grainless homogeneous crystal screen such as that described in Carlson U.S. Pat. No. 3,917,950, placed as close to the outside of the pipe as protection against physical damage will permit. With a fluorescent screen of about 20 cm width, the X-ray tube can be placed with its focal spot some 25 cm from the screen, which permits a high contrast sharp image to be obtained through the walls of pipes 3 cm or more in thickness. In general the X-ray source should be spaced from the test object at least several times the size of the focal spot.

Facing the screen 15 in a light tight chamber 16 is preferably a 45° mirror 17 reflecting the X-ray shadow picture from the fluorescent screen 15 into the optical axis of an image-isocon video camera 18 so located that the sensitive camera is safely outside of the X-ray beam. It is preferred that the chamber 16 be twice as long as the distance from the fluorescent screen 15 to the mirror 17 and be provided with a test pattern 19 which can be selectively illuminated by a lamp 20 facing the test pattern 19. For adjustment of the camera 18 the lamp 20 illuminates the test pattern and the mirror 17 is turned to a position at a right angle to its operating position as shown in the drawing, to reflect the test pattern into the camera 18. The camera and housing assembly is provided with an optical focus screw 21 for precise adjustment of the distance from the optical lens 22 through the mirror 17 to the test pattern 19 and therefore also through the mirror 17 in its alternate position to the fluorescent screen 15 since the mirror is mounted exactly halfway between the test pattern and the screen. This feature permits convenient and rapid adjustment of the camera for optimum sharpness and contrast at any time during the use of the equipment.

The video camera 18 is preferably an intensified image-isocon of high resolution. It has one or more stages of light intensifier coupled to it by a fiber optics element. The video camera is preferably equipped for selective operation at a borizontal scan of either 525 or 1029 lines and a vertical scan of 30 frames per second interlaced 2 to 1. If desired it may also be equipped for electronic zoom operation by reduction of the camera raster size.

Figure 4:
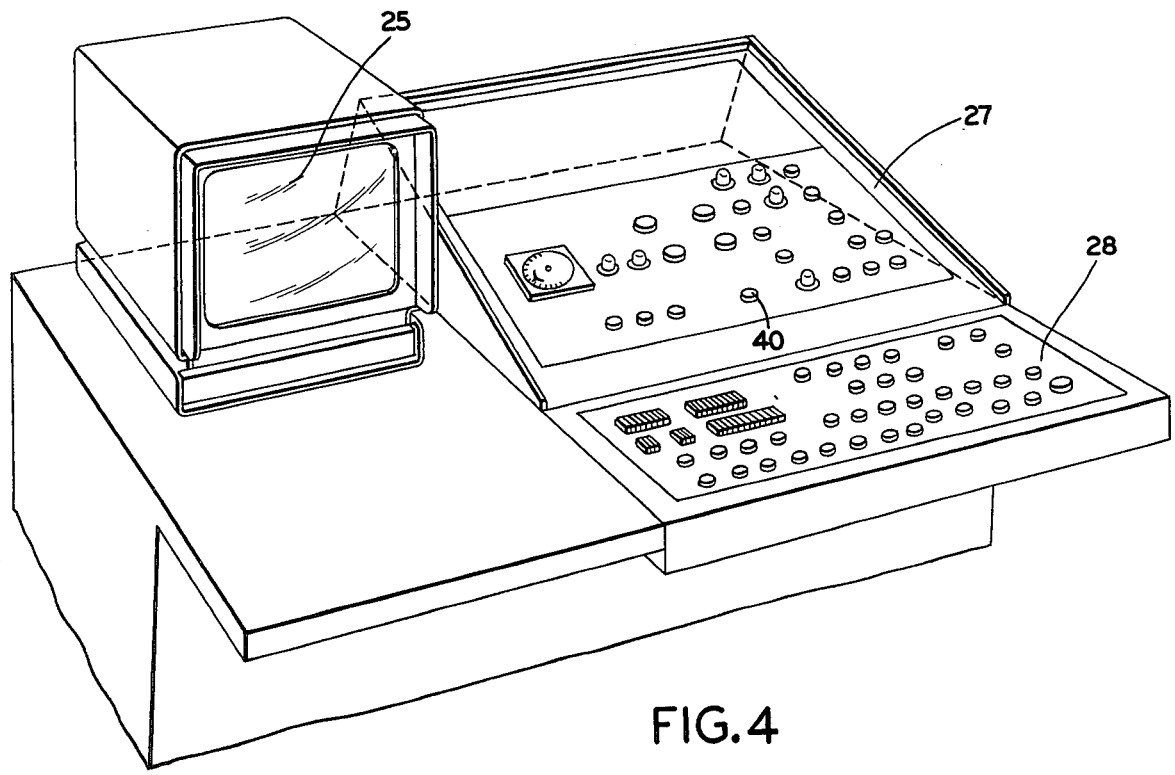
FIG. 4 shows a suitable arrangement of the operator's console.

The video camera 18 is connected to a picture tube monitor 25 on the operator's pulpit 26, beside the operator's console 27, as shown in FIG. 1 and FIG. 4. The monitor permits continuous observation of the X-ray shadow picture of the weld as the pipe 23 is steadily advanced with the weld between the fluorescent screen 15 and the X-ray tube 14 on the boom 13.

Figure 5:
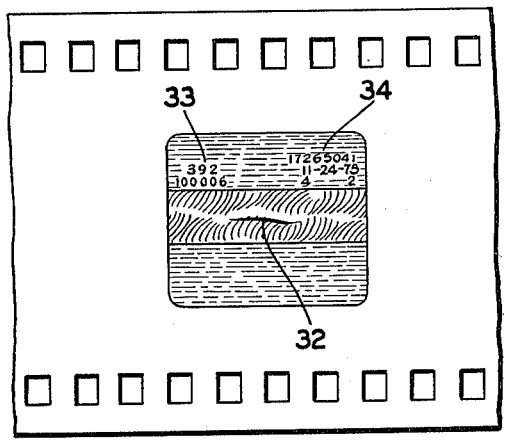
FIG. 5 is a representation of the kind of visual signal produced and recorded by this invention.

The pulse generator coupled to carriage drive motor 24 is connected to the control equipment in the operator's console 27, and specifically to one of several data generators 28. This causes appearance on monitor 25 of numbers 33 indicating the momentary distance of the X-ray axis from the end of the pipe being examined. Other data generators are provided on the console for manual operation by thumbwheels to cause display on the monitor of other data 34 such as serial number, size, time, operator's identification, and the like. All such data can be photographed on 35 mm film, for a permanent record, as shown in FIG. 5, and as will be further explained below.

The equipment so far described may be operated either with or without an additional inspection device such as an ultrasonic transducer or transducers. If an ultrasonic unit 30 is employed, it can be used to indicate to the operator the presence and location of an irregularity so that the operator can make a careful X-ray examination of the site to determine whether there is an actual flaw in the weld.

The ultrasonic unit 30 may be any of the well known devices containing high frequency sound transducers capable of sensing the presence of discontinuities.

Figure 3:
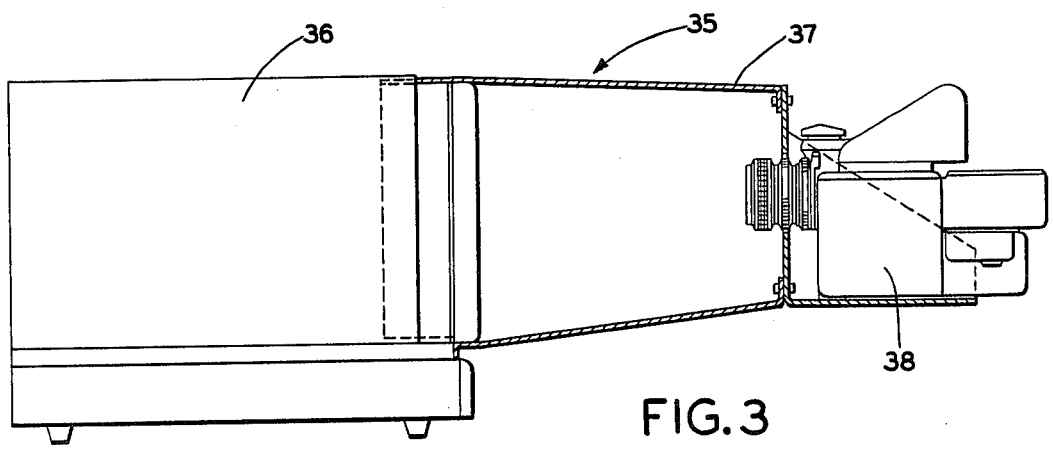
FIG. 3 is a view of the photographic camera for permanently recording the entire length of weld or such portions as may contain flaws.

Whether or not an ultrasonic device is used, the equipment of this invention may be provided with an auxiliary recording device 35, shown in FIG. 3, for a temporary or permanent record of the X-ray image of the weld which is being inspected, on photographic film or other suitable recording medium such as magnetic tape.

Preferably the recording unit 35 will be activated only to make a record of specific locations where some kind of irregularity is indicated. For this purpose the recording unit 35 will preferably contain a slave monitor 36 having a video picture tube coupled inside of a light tight chamber 37 with a photographic camera 38 of the type which will take a picture of the view facing it when electrically activated and then automatically advance the film to another frame.

This photographic camera can be programmed for recording the shadow picture at intervals slightly less than the time required for a spot to pass across the picture tube of the monitor, for a complete and inexpensive pictorial record. Alternatively, it can be arranged for manual operation to record only those zones in which a special situation appears to exist.

The operator at his console can determine either from observation of the X-ray shadow picture on his monitor 25 or from receipt of a signal from the ultrasonic unit 30 that an event which should be recorded exists and if he has not already done so, he will then activate data generators 28 for generating and transmitting to both of the monitors or at least monitor 36 such signals as will produce a visual code to identify the work piece, the location on the work piece such as distance from one end, and whatever other information may be useful in subsequent handling and possible repair of the work piece, alongside of the image of the X-ray shadow picture. The operator will then be able to activate the camera 38 by a suitable control 40 on the console.

The combination of X-ray and ultrasonic scanning of the longitudinal weld permits very convenient, rapid, and effective location of imperfections in the weld, since discontinuities can be detected by the reflection of the high frequency sound, whether or not an actual void is present, whereas X-rays will generally detect only voids or inclusions of low density material.

The ulrasonic equipment can then be arranged so that a response above a predetermined magnitude will give the operator a warning that a probable discontinuity exists so that he can be on the lookout to see whether it is confirmed by an irregularity in the shadow picture in the monitor.

Figure 6:
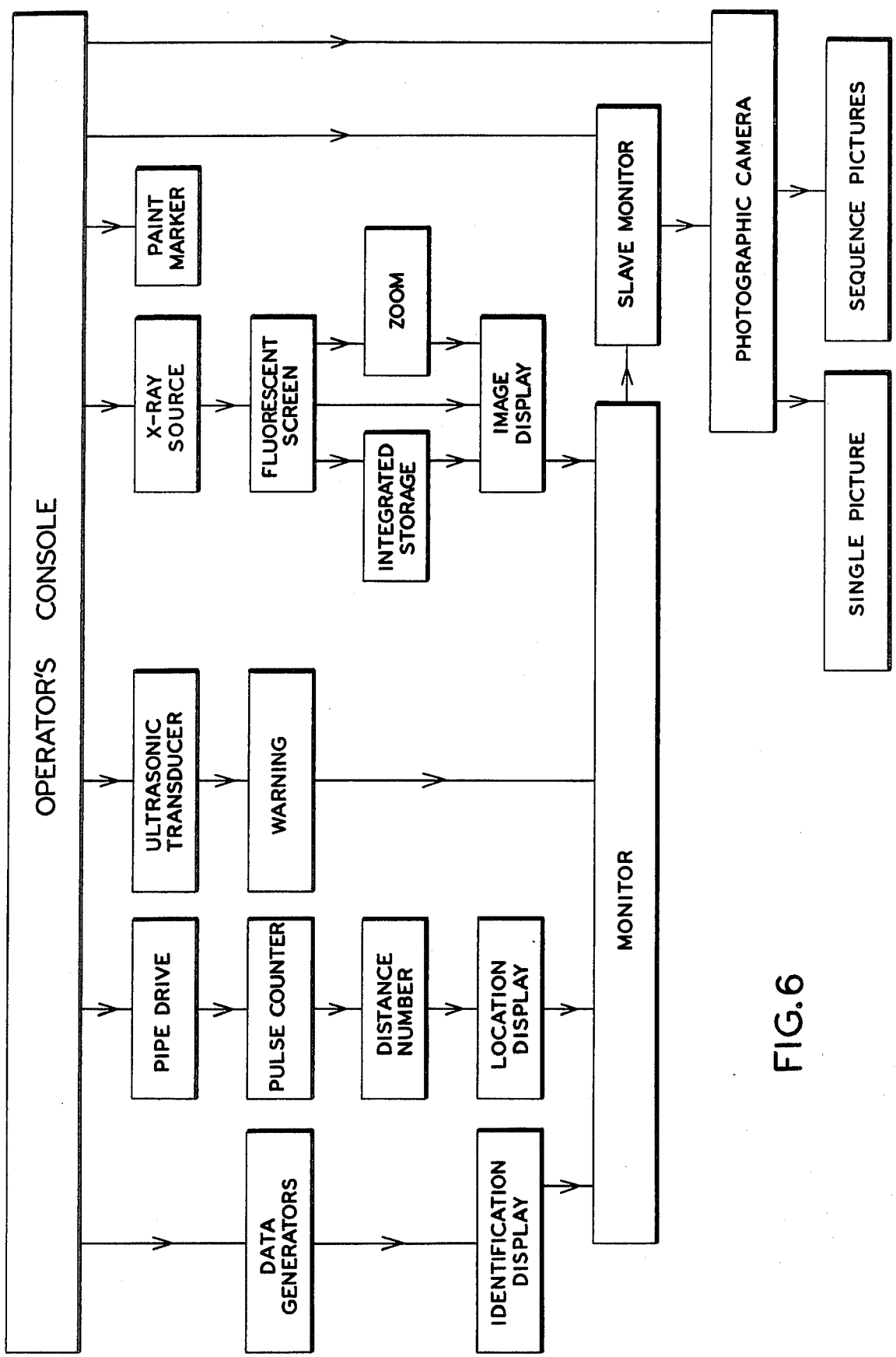
FIG. 6 is a diagram of the interrelationships among the various units which make up the invention.

The operator thus warned can stop the progress of the pipe, enhance the contrast of the picture by integration in a storage tube, as indicated in the diagram of FIG. 6, and transfer the image to the slave monitor 36 for further enhancement of contrast by integration on the film of camera 38, before completing inspection. The photograph, including the picture of the flaw and its distance from the end of the pipe, can then be used for locating the flaw at a repair station so that the bad portion can be cut out and rewelded. In addition, the operator can activate a paint marker before resuming inspection.

After repair of the work piece, it can be reinspected and the X-ray picture can be compared with the photographic record of the first inspection and, if desired, an additional photograph may be made and preserved as a record of the condition of the work piece before and after repair.

The versatility of the apparatus described above, and the many variations of procedure which it permits, are indicated in the functional diagram in FIG. 6, from which it is apparent that the apparatus in its preferred form permits rapid mechanized examination of welds with two different inspection procedures automatically checking each other, and permits simple and inexpensive but complete pictorial identification of flaws for easy location and repair.

I claim:

1. A machine for nondestructive testing of welds, comprising:

a. means for mechanically traversing the length of a weld on one side of the test object with a source of X-rays;
b. on the other side of the object, and close to it, in the beam of the radiation, a grainless sheet of fluorescent material sensitive to X-rays;
c. a video camera coupled to the fluorescent screen;
d. a picture tube for display of the image transmitted by the video camera;
e. data generators for superimposing identifying indicia on the picture in the picture tube; and
f. means for recording the composite of the indicia and the picture in the picture tube.

2. A machine as in claim 1 in which the video camera is an image-isocon equipped with at least one stage of electronic light intensification.

3. A machine as in claim 1, including means for integrating at least several frames from the picture tube to produce a record of an integrated image.

4. A machine as in claim 1, including an ultrasonic transducer coupled to the object at the location of the weld, and means for presenting to an operator a warning of the presence of a sonic discontinuity in the weld.

5. A machine as in claim 4, including means for integrating at least several frames from the picture tube to produce a record of an integrated image.

6. A machine as in claim 5, in which the means for integrating includes a storage tube, and the means for recording is connected to receive the integrated image in the storage tube.

7. A machine as in claim 6, in which the means for recording includes a photographic camera set for an exposure time extending over several video frames.

8. A machine as in claim 7, including means for limiting the duration of the ultrasonic warning to the time in which the ultrasonic response is of a magnitude indicative of a flaw.

9. A machine as in claim 8, including means for integrating at least several frames from the picture tube to produce an integrated image.

10. A machine as in claim 9, including a photographic camera set for an exposure time extending over several video frames.

11. A method for nondestructive testing of welds, comprising:
a. subjecting the welds to penetrating X-rays;
b. intercepting the radiation by a grainless fluorescent screen to form a shadow picture;
c. displaying the shadow picture by means of a video camera on a picture tube;
d. simultaneously displaying on the picture tube identifying indicia for the shadow picture, and
e. recording the composite of the indicia and the picture.

12. A method as in claim 11, in which the light from the shadow picture traverses a light intensifier before entering the video camera.

13. A method as in claim 11, in which electronic noise is minimized by integration of frames of the shadow picture before display on the picture tube.

14. A method as in claim 13, in which the identifying indicia displayed on the picture tube include alphanumeric symbols supplied by an operator.

15. A method as in claim 14, in which an ultrasonic transducer warns the operator of the presence of a sonic discontinuity.

* * * * *